United States Patent [19]
Goymann et al.

[11] Patent Number: 4,795,470
[45] Date of Patent: Jan. 3, 1989

[54] TWO-PART SOCKET FOR HIP-JOINT PROSTHESIS

[76] Inventors: Volkmar Goymann, Forstmannstr. 62, D-4300 Essen 16; Emmanuel Anapliotis, Tollensestr. 16, D-1000 Berlin 37, both of Fed. Rep. of Germany

[21] Appl. No.: 487,185
[22] Filed: Apr. 21, 1983
[51] Int. Cl.⁴ .............................................. A61F 2/32
[52] U.S. Cl. ......................................... 623/22; 623/18
[58] Field of Search ....................... 3/1.9, 1.51, 1.912, 3/1.513; 128/92 C, 92 CA; 623/16, 18, 20, 22, 23

[56] References Cited

U.S. PATENT DOCUMENTS

| | | | |
|---|---|---|---|
| 3,820,167 | 6/1974 | Sivash | 623/22 |
| 3,840,904 | 10/1974 | Tronlo | 623/22 |
| 3,918,102 | 11/1975 | Eichler | 623/22 |
| 4,101,985 | 7/1978 | Baumann et al. | 128/92 CA |
| 4,437,193 | 3/1984 | Oh | 3/1.912 |

FOREIGN PATENT DOCUMENTS

| | | | |
|---|---|---|---|
| 2625529 | 12/1977 | Fed. Rep. of Germany | 623/16 |
| 2645101 | 4/1978 | Fed. Rep. of Germany | 623/22 |
| 2839661 | 9/1979 | Fed. Rep. of Germany | 623/22 |
| 2911754 | 10/1980 | Fed. Rep. of Germany | 623/22 |
| 2950536 | 7/1981 | Fed. Rep. of Germany | 3/1.912 |
| 3101333 | 12/1981 | Fed. Rep. of Germany | 623/22 |
| 1287526 | 2/1962 | France | 128/920 A |

OTHER PUBLICATIONS

"The Art of Total Hip Arthroplasty", William Thomas Stillwell, published by Harcourt Brace Jovanovich.
Girard "La Proshese Universelle De Lord", Catalog-Division of Howmedica, printed in France 1979.

Primary Examiner—Richard J. Apley
Assistant Examiner—David J. Isabella
Attorney, Agent, or Firm—Spencer & Frank

[57] ABSTRACT

A prosthetic hip-joint socket for mounting in a cavity in a hip bone has an outer part having a generally part-spherical outer surface formed with a screwthread and an inner part complementarily fittable inside the outer part and having an acetabulum-forming recess. The outer part is of generally the same elasticity and deformability as the bone it is mounted in. In addition the inner part is received with slight play in the outer part. The screwthread is formed by a succession of thread-cutting teeth each having a relieved outer edge, with each cutting edge being spaced most from the axis at its leading end and arcing smoothly toward the axis back from this leading end toward its trailing end. The outer part is formed with an inner generally frustoconical surface centered on the axis and the inner part has a complementary surface engageable therewith.

19 Claims, 2 Drawing Sheets

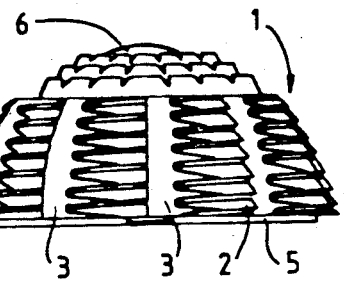
Fig. 1
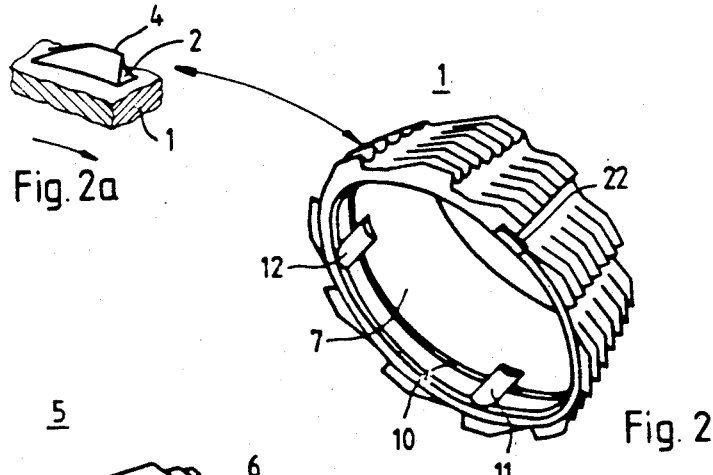
Fig. 2a
Fig. 2
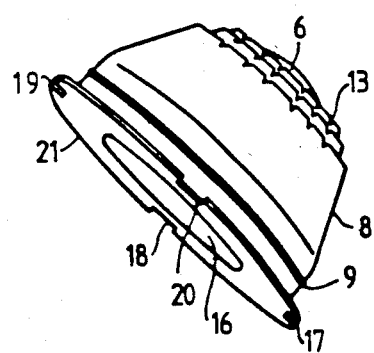
Fig. 3
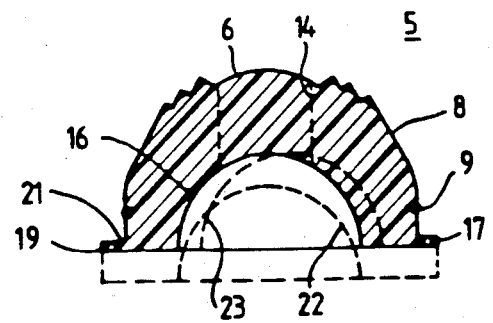
Fig. 4

TWO-PART SOCKET FOR HIP-JOINT PROSTHESIS

FIELD OF THE INVENTION

The present invention relates to a prosthetic hip. More particularly this invention concerns the socket of a total or partial hip-joint prosthesis.

BACKGROUND OF THE INVENTION

A standard type of prosthetic hip-joint socket has an outer support part that is anchored in an appropriately formed recess in the hip joint, and an inner part or insert that fits into this support part and that itself forms the new acetabulum. This two-part construction makes it possible to use a standard-size outer part, and to have a whole set of inserts formed with differently sized acetabulum-forming recesses to accommodate different shaft balls.

French patent document No. 2,099,259 describes such an outer part which has a pin-shaped extension formed with a screwthread. The pelvis must be specially bored out to receive this element and its extension, with considerable destruction of bony tissue. The cavity that is cut in the pelvis for this outer part must be exactly positioned, as the support fits complementarily in it in only one orientation.

Another system is seen in German patent document No. 2,411,617 into which the insert can be snapped. The outer surface of the support is tapered and formed with a screwthread. As in the above-described system, such an arrangement requires that a particularly shaped cavity be formed, and then threaded. The outer support part can only sit in one orientation, normally relative to a central axis or the cavity, in the outer part, so once again this cavity must be formed with enormous care. No adjustment of the orientation of the artificial acetabulum is possible once the cavity for the outer part has been formed in the hip bone.

OBJECTS OF THE INVENTION

It is therefore an object of the present invention to provide an improved socket for a prosthetic hip joint.

Another object is the provision of such a socket for a prosthetic hip joint which overcomes the above-given disadvantages, and that in particular allows some adjustment of the position of the new acetabulum once the socket has been emplaced.

Yet another object is to provide an improved method of fitting a prosthetic socket into a hip bone which allows the surgeon to damage minimal bone tissue, to work fast, and still to have the opportunity of adjusting the position of the new acetabulum at several stages.

SUMMARY OF THE INVENTION

These objects are attained according to the instant invention in a prosthetic hip-joint socket for mounting in a cavity in a hip bone which has an outer part having a generally part-spherical outer surface formed with a screwthread and an inner part complimentarily fittable inside the outer part and having an acetabulum-forming recess.

With this system, therefore, the outer part can be mounted in any orientation inside the cavity, since the semispherical surface fits in any centered position therein. The invention is based on the recognition that force transmission in the hip bone is mainly central in the acetabulum, in line with the leg. Thus when according to this invention the outer part is annular and the inner part is cup-shaped and has a closed inner end forming when the two parts are fitted together a smooth generally semispherical continuation of the outer surface of the outer part there is direct force transmission between the insert and the hip bone, not indirect transmission through the outer part.

The outer part according to the invention is of generally the same elasticity and deformability as the bone it is mounted in. In addition the inner part is received with slight play in the outer part. Thus the outer part will not work against the bone, and if it does deform a little will not interfere with the fit of the trochanter ball in the new acetabulum of the inner part.

The screwthread in accordance with this invention is formed by a succession of thread-cutting teeth each having a relieved outer edge, that is with each cutting edge being spaced most from the axis at its leading end and arcing smoothly toward the axis back from this leading end toward its trailing end. For best clearing action the outer part is also formed with transverse relief grooves.

In accordance with another feature of this invention the outer part is formed with an inner generally frustoconical surface centered on the axis and the inner part has a complementary surface engageable therewith. Thus the inner surface extends at least partially generally perpendicular to the normal direction of force from a femur having a ball in the recess. Force transmission will always be surface-to-surface for minimal point stress.

With the system of this invention the expensive outer part, normally made of a costly metal like titanium, need only be stocked by the hospital in a few different sizes. The less expensive, normally plastic, inner part can be stocked in a wide variation of sizes that together with the outer part allows any size patient to be accommodated. Some of the inserts can have recesses off center to the axis. This makes it possible to carry out fine adjustment that can even compensate for hitherto incurable congenital deformities where the old acetabulum is malpositioned.

To secure the parts against relative movement once assembled, they have formations that radially interengage in predetermined positions when the parts are fitted together. These formations can be radially interfitting tabs and notches inside the outer part or provided on a rim thereof. Thus the outer part can be secured in place without the use of cement and the inner part can be fixed therein without adhesive also.

The method of the instant invention therefore lies principally in the step of forming a substantially partspherical cavity in the hip bone at the site of the old acetabulum. A standard ball-type milling head can be used, and most of the difficulties of exactly forming this recess are avoided. Thus the outer socket part can fit in any of a plurality of different positions inside the partspherical cavity. The installation procedure is simplified when the outer part is formed with thread-cutting teeth. Thus the outer part is forcibly screwed into the cavity to cut its own threads in the bone.

In addition as mentioned above the outer part is annular and the inner part is cup-shaped and has a closed inner end forming when the two parts are fitted together a smooth generally semispherical continuation of the outer surface of the outer part. This inner end engages directly against the bottom of the cavity when the two parts are fitted together. The inner end is formed with bumps that seat solidly against the spongy interior of the hip bone, solidly positioning this insert.

DESCRIPTION OF THE DRAWING

The above and other features and advantages will become more readily apparent from the following, reference being made to the accompanying drawing in which:

FIG. 1 is a side view of a hip-joint socket according to this invention;

FIG. 2 is a perspective view of the outer part of the socket of FIG. 1;

FIG. 2a is a large-scale view of a detail of FIG. 2;

FIG. 3 is a perspective view of the inner part of the socket of FIG. 1;

FIG. 4 is an axial section through the insert of FIG. 3;

SPECIFIC DESCRIPTION

Figure 5:
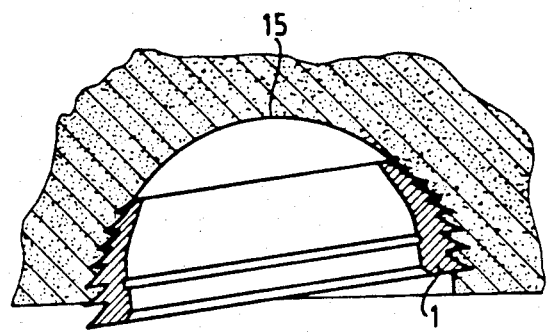
FIGS. 5 and 6 are sectional views illustrating installation of the outer part of FIG. 2.

As seen in FIGS. 1 through 4 a prosthetic hip-joint socket according to this invention has a metallic, normally titanium, outer part or support 1 of relatively thin wall thickness and a synthetic-resin, e.g. polytetrafluoroethylene, inner part or insert 5. The two parts 1 and 5 are centered on a main axis A and fit complimentarily together.

The outer part 1 seen in FIGS. 1 and 2 is annular and has an outer surface of part-spherical, here nearly semispherical, shape, that is lying on the surface of an imaginary sphere whose center is on the axis A, and formed with a screwthread 2 itself constituted by one or more helical rows of teeth 4 separated by lands or relief grooves 3. At its wider end the outer part 1 is formed with several angularly equispaced and radially outwardly projecting centering tabs 12. The wall thickness of this part 1 is such that it deforms about the same as bone, so it will seat solidly therein and not work against the bone when there is some stressing. In addition the ring 1 has an overall axial length which is equal to or smaller than the inner diameter of this part 1.

Each of the teeth 4 as shown in some detail in FIG. 2a has, in a rotation insertion direction D about the axis A, a sharp upper edge which moves radially in from its leading end. Thus these teeth 4 are capable of cutting their own threads in bone without clogging and jamming. The teeth 4 are milled in the surface of the metal ring from which the part 1 is made in two operations, the crosswise relief grooves 3 and relief angles on the teeth 4 being created in the second milling operation.

Internally the outer part 1 is formed with a frustoconical surface 7 centered on and extending at 45° to the axis A, a radially inwardly open circumferential groove 10 also centered on this axis A, and three short grooves 11 that open axially only in one direction, here toward the wide end of the ring 1. A tool rotatable about the axis A fits into these grooves 11 to solidly support the outer part 1 and allow it to be forcibly screwed into a cavity formed as described below in a hip bone, normally at the site of a damaged acetabulum which is enlarged for reception of the socket liner according to this invention.

The insert 5 as shown in FIG. 3 is shaped to fit into the outer part 1, having a frustoconical outer surface 8 complementary to the surface 7. It has a normally closed inner end 6 that is formed with rings of bumps 13 that engage against the floor of a cavity in which the insert 1 is seated. This outer end 6 is of part-spherical shape centered on the axis A so that when the parts 1 and 5 fit together their outer surfaces together form a nearly perfect semisphere. At its other end the insert 5 is provided with an annular outwardly projecting spring wire 9 adapted to snap into the groove 10 when the two parts 1 and 5 are fitted together, and a rim 21 that projects radially outwardly and that is formed with four angularly equispaced and outwardly open notches 16, 17, 18, and 19. When the two parts 1 and 5 are firmly seated together the tabs 12 can engage in the notches 17-20 to lock them against relative rotation about the axis A.

In addition this part 5 may be formed with one or more small bumps or other formations 26 that can fit into the notches 11 to lock the two pieces angularly with respect to each other. Positioning marks can also be provided at the front end of the frustoconical portion 8 instead of the ring 9.

Internally the cup-shaped insert 5 is formed with a semispherical seat 16 suitable either to receive the normally metal ball of the other half of the prosthetic hip joint, or the patient's own ball. This seat 16 can be axially further cut out as indicated at 22 or off center as shown at 23. Thus it is possible to coarsely position the outer part 1 and then to select an appropriate insert 5 that finely positions the seat for the joint ball. This allows the surgeon to work much faster, thereby cutting the patient's exposure to complications. In addition this ability to finely position the ball seat relative to the cavity milled in the hip joint at the site of the patient's unusable acetabulum allows even congenital deformations to be corrected.

FIG. 4 indicates how a window 14 can be formed in the end 6 of the insert 5 to allow verification of proper seating of the insert 5 with its bumps 13 against the floor of the cavity holding the socket 1, 5.

Figure 6:
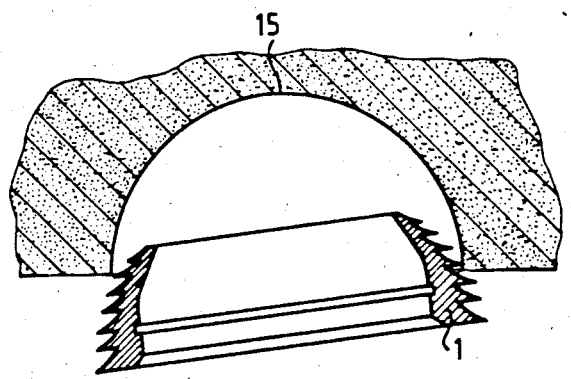

FIGS. 5 and 6 indicate how a hip bone is formed with a semispherical cavity 15 whose center of curvature lies near but not necessarily at the desired location for the ball-receiving seat. An outer part 1 is screwed into this cavity as indicated in FIG. 5 in approximate orientation with axis A as close as possible to the desired center for the seat 16. Thus this axis A can be other than perpendicular to the bone surface at the installation point, so long as it passes through the center of curvature of the cavity 15.

Figure 7:
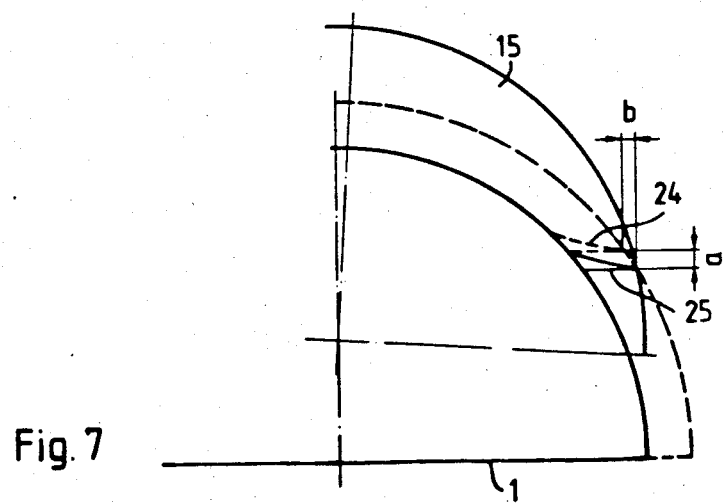
FIG. 7 is a large-scale diagram illustrating principles of this invention.

FIGS. 6 and 7 illustrate how the outer part 1 is screwed into the cavity 15. The triangles 24 and 25 represent the lending and trailing ends of a thread segment whose outer cutting edge is not cut back or relieved as shown in FIG. 2a. As a result of the pitch of the thread section the front edge 24 of the thread will therefore be as shown in dashed lines further along on the axis A than the trailing edge 25. With a height difference a as a result of the pitch the leading or cutting edge is spaced by a distance b from the surface of the semispherical cavity 15 while the noncutting trailing edge 25 engages it. This would plainly lead to scraping or jamming of the part 1 in the cavity 15, unlike the system of this invention where the relieved teeth 4 will not clog or jam, and the cavity 15 need not be tapped in advance.

With this system therefore a bad acetabulum can be milled out with a standard round milling tool without any particular worry about exact positioning, and with minimal damage to bone. The outer part 1 is then forcibly screwed into the semispherical cavity 15 thus formed with its axis A in line with the main direction force is to be exerted in, that is in line with the main part of the femur. The teeth 4 will cut their own threads and the part 1 can be expected to seat solidly in the cavity, even if its axis A is not perpendicular to the bone surface around the cavity 15. The position of the part 1 can be verified easily simply by looking into it as the base of the cavity 15 will remain exposed. The teeth 4 will hold solidly in the hard outer part of the bone, the so-called corticalis while the bumps 13 will engage against the spongiosa and therefore have a very solid seat.

Thereupon exact measurements are made and an insert 5 is selected from a whole set of inserts with differently dimensioned and oriented acetabulum-forming recesses 16. This element is snapped into place and the new socket is complete. The rear end 6 of the insert 5 engages directly through the ring 1 against the bone of the pelvic girdle, thereby relieving the screwthread 2 of transmitting all of the force. The part 1 is constructed so that it can deform slightly right along with the hip bone if necessary and the synthetic-resin insert is a slightly loose fit in it so such deformations will not be harmful to the new socket.

This socket can be part of a total hip-joint prosthesis so that a normally metallic ball fitted to the top of the femur is fitted in its recess. It can also snap over the natural ball of the patient's femur if it is usable.

I claim:

1. A support member for a prosthetic hip joint socket for mounting in a cavity of at least approximately hemispherical form in a hip bone, said support member having an outer surface which has the shape of a spherical segment having a radius of curvature originating from a single point so that said segment lies on the surface of an imaginary sphere having a center at said single point, said support member being formed with a self-tapping screw thread which is composed of a succession of thread-cutting teeth projecting from said outer surface so that said outer surface constitutes the root of said teeth, said thread being centered on an axis about which said support member is rotatable for screwing said thread into the cavity, said outer surface having a radius of curvature substantially corresponding to that of the cavity, whereby said support member is positionable within the cavity in any one of a plurality of different orientation positions, said support member being formed to receive an inner part complimentarily fittable into said support member.

2. A support member as defined in claim 1 which has an annular form with a large diameter base and a small diameter base, which bases are spaced apart, along the axis, by a distance which is no greater than the diameter of said support member at said small diameter base.

3. A support member as defined in claim 2 which has a wall thickness and elasticity constant selected for giving said support member generally the same elasticity and deformability as the bone in which the socket is to be mounted.

4. A support member as defined in claim 1 wherein: each said thread-cutting tooth has a leading end and a sharp outer edge extending from said leading in the direction in which said outer part is rotatable; each tooth having a trailing end which is spaced from the associated leading end such that during screwing of said outer part into the cavity the leading end is forward of the trailing end; and said outer edge of each tooth follows a path which extends toward the axis from the leading end toward the trailing end of the tooth.

5. A support member as defined in claim 1 having an inner generally frustoconical surface for receiving the inner part, and the inner part is insertable into said support member after said support member has been screwed into the hip bone cavity.

6. A support member as defined in claim 5 wherein the inner part has a recess for supporting a femur ball, and said inner surface of said support member extends at least partially generally perpendicular to the normal direction of force from a femur having a ball in the recess.

7. A system for forming a prosthetic hip joint socket for supporting a femur ball, comprising: a support member as defined in claim 1; and a plurality of inner parts each formed to fit complimentarily into said support member and each having a recess for receiving such femur ball, said recess having a respectively different location in each said inner part.

8. A prosthetic hip joint socket comprising a support member as defined in claim 1; and an inner part containing a recess for supporting a femur ball.

9. A socket as defined in claim 8 wherein said recess is eccentric to the axis.

10. A socket as defined in claim 8 wherein said support member and said inner part have formations that radially interengage in predetermined positions when said inner part is fitted into said support member.

11. A socket as defined in claim 8 wherein: said support member has an inner generally frustoconical surface for receiving said inner part; said inner part has an outer surface complementary to said inner surface; said inner part is provided with structures protruding from said outer surface; and said support member is provided at said inner surface with recesses for receiving a tool during screwing of said support member into a hip bone cavity, and for receiving said structures protruding from said outer surface of said inner part.

12. A socket as defined in claim 8 wherein said inner part is cup-shaped and has a closed inner end forming, when said inner part is inserted into said support member, a hemisphere with said outer surface of said support member.

13. A socket as defined in claim 12 wherein the hip bone has spongiosa in the region of the cavity and said inner end of said inner part has a structure adapted to the spongiosa.

14. A socket as defined in claim 13 wherein said structure at said inner end has the form of grooves oriented at right angles to one another.

15. A socket as defined in claim 12 wherein each said tooth has a leading end, a trailing end and a sharp outer edge extending from said leading end to said trailing end and relieved in the region of said trailing end.

16. A socket as defined in claim 15 wherein said teeth are disposed in groups spaced apart about the axis, and said outer surface has portions defining transverse relief grooves between successive groups of teeth.

17. A socket as defined in claim 8 wherein said recess in said inner part is formed to snap over a femur ball for immediate securing of such ball to said socket.

18. A support member as defined in claim 1 wherein each said tooth has a leading end, a trailing end and a sharp outer edge extending from said leading end to said trailing end and relieved in the region of said trailing end.

19. A support member as defined in claim 18 wherein said teeth are disposed in groups spaced apart about the axis, and said outer surface has portions defining transverse relief grooves between successive groups of teeth.

* * * * *